United States Patent [19]

Schulz et al.

[11] Patent Number: 4,626,544

[45] Date of Patent: Dec. 2, 1986

[54] AZOLE COMPOUNDS AND FUNGICIDES CONTAINING THESE COMPOUNDS

[75] Inventors: Guenter Schulz, Ludwigshafen; Hubert Sauter, Mannheim; Gernot Reissenweber, Boehl-Iggelheim; Eberhard Ammermann, Ludwigshafen, all of Fed. Rep. of Germany

[73] Assignee: BASF Aktiengesellschaft, Fed. Rep. of Germany

[21] Appl. No.: 727,136

[22] Filed: Apr. 25, 1985

[51] Int. Cl.[4] .................... A01N 43/50; A01N 43/653; C07D 233/60; C07D 249/08

[52] U.S. Cl. .................................... 514/383; 514/183; 514/399; 548/101; 548/262; 548/341

[58] Field of Search ........................ 548/101, 262, 341; 514/183, 383, 399

[56] References Cited

U.S. PATENT DOCUMENTS 4,086,351 4/1978 Babasulramanyan et al. ..... 424/269

FOREIGN PATENT DOCUMENTS 3209431 9/1983 Fed. Rep. of Germany .

1318590 5/1973 United Kingdom .

*Primary Examiner*—Richard L. Raymond

*Attorney, Agent, or Firm*—Keil & Weinkauf

[57] ABSTRACT

Azole compounds of the formula

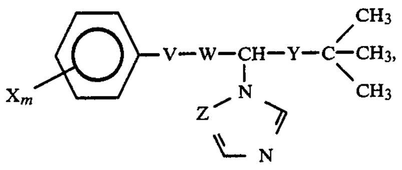

I where V is oxygen or sulfur, X is hydrogen, halogen, alkyl, alkoxy, trifluoromethyl, phenyl or phenoxy, m is an integer from 1 to 5, W is an olefin group which is unsubstituted or substituted, or is alkynyl, Z is CH or N, and Y is C═O or $CR^3OR^4$, where $R^3$ is hydrogen, alkyl, alkenyl or alkynyl, and $R^4$ is hydrogen, alkyl, alkenyl, alkynyl or alkanoyl, and their plant-tolerated addition salts with acids and metal complexes, and fungicides which contain these compounds.

4 Claims, No Drawings

AZOLE COMPOUNDS AND FUNGICIDES CONTAINING THESE COMPOUNDS

The present invention relates to novel, useful azole compounds, a process for their preparation, fungicides containing these compounds and their use as fungicides.

It has been disclosed that imidazole derivatives, eg. 1-[2-(2,4-dichlorophenyl)-2-(2-propenyloxy)-ethyl]-1H-imidazole (British Pat. No. 1,318,590), possess good fungicidal activity. However, the action is not always satisfactory at low application rates and concentrations. Moreover, the fungitoxic action is often associated with high phytotoxicity, so that the crops are also damaged at the concentrations required for controlling fungi, for example rusts, in crops. For these reasons, they are in some cases unsuitable for use as crop protection agents for controlling fungi.

We have found that azole compounds of the formula

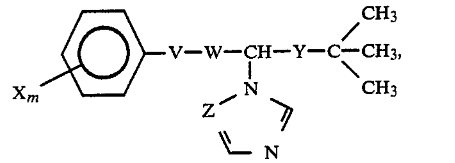

I where V is oxygen or sulfur, X is hydrogen, fluorine, chlorine, bromine, $C_1$–$C_4$-alkyl, $C_1$–$C_4$-alkoxy, trifluoromethyl, phenyl or phenoxy, m is an integer from 1 to 5, the individual atoms or groups being identical or different when m is greater than 1, W is a group of the formula $(CH_2)_v—CR^1═CR^2—(CH_2)_t$, where $R^1$ and $R^2$ are identical or different and are each hydrogen, methyl, ethyl, chlorine or fluorine, or is a group of the formula $(CH_2)_v—C≡C—(CH_2)_t$, and v and t are identical or different and are each 1, 2 or 3, Z is CH or N, and Y is C═O or $CR^3OR^4$, where $R^3$ is hydrogen, methyl, vinyl, allyl, ethynyl or propynyl, and $R^4$ is hydrogen, $C_1$–$C_4$-alkyl, $C_2$–$C_4$-alkenyl, $C_2$–$C_4$-alkynyl or $C_2$–$C_4$alkanoyl, and their plant-tolerated addition salts with acids and metal complexes, have a very good fungicidal action coupled with excellent toleration by plants.

In the compounds of the formula I, the azolyl-substituted carbon atom and the adjacent carbon atom substituted by oxygen are chiral. Accordingly, the active ingredients are obtained as enantiomer mixtures which can be separated into the optically active enantiomers. In general, because of the presence of two chiral centers, the active ingredients also occur as diastereomer mixtures, which can be separated into the individual components in a conventional manner, for example by crystallization or chromatography. However, separation of the enantiomers or diastereomers is not usually required in order to use the compounds as fungicides. The double bond can have a cis or trans configuration. The invention embraces the mixtures, including the cis/trans mixtures, as well as the sterically or optically active pure substances.

The phenoxy or thiophenoxy radical can, for example, be substituted by the following radicals $X_m$: hydrogen, 2-fluoro, 4-fluoro, 2-chloro, 3-chloro, 4-chloro, 4-bromo, 2,4-dichloro, 2,4,6-trichloro, 2-methyl, 3-methyl, 4-methyl, 4-n-propyl, 4-tert.-butyl, 4-n-butyl, 3-trifluoromethyl, 4-trifluoromethyl, 4-phenyl, 4-methoxy, 4-butoxy or 4-phenoxy.

m is, for example, 1, 2 or 3.

$R^1$ and $R^2$ are each, for example, hydrogen, methyl or chlorine, and the double bond has a cis or trans configuration, preferably a trans configuration.

Accordingly, examples are:

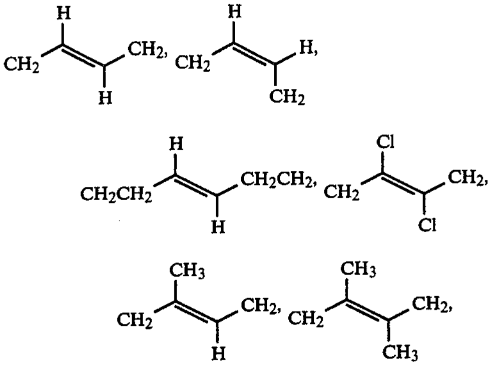

$CH_2—C≡C—CH_2$, $CH_2CH_2—C≡C—CH_2CH_2$.

$R^3$ is, for example, vinyl, allyl, ethynyl or propynyl, and $R^4$ is, for example, hydrogen, methyl, ethyl, n-propyl, prop-2-en-1-yl, prop-2-yn-1-yl, n-butyl, 2-methylprop-2-en-1-yl, acetyl, propionyl, butyryl or isobutyryl.

Examples of suitable addition salts with acids are the chlorides, bromides, sulfates, nitrates, phosphates, acetates, oxalates and dodecylbenzenesulfonates. The activity of the salts is attributable to the cation, so that any anion may be chosen provided that it is plant-tolerated.

Suitable metal complexes are compounds of the formula

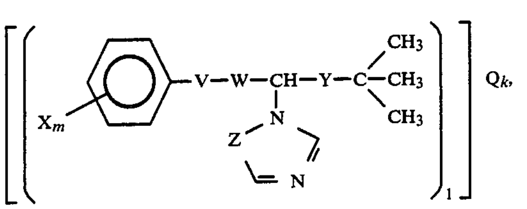

V where $X_m$, V, W, Z and Y have the above meanings and Me is a metal, eg. copper, zinc, tin, manganese, iron, cobalt or nickel, Q is the anion of an inorganic acid, eg. hydrochloric acid, sulfuric acid, phosphoric acid or hydrobromic acid and l and k are each 1, 2, 3 or 4.

The azolyl compounds of the formula I as claimed in claim 1 in which $R^3$ is hydrogen are preferably prepared by stereoselective reduction of a ketone of the formula

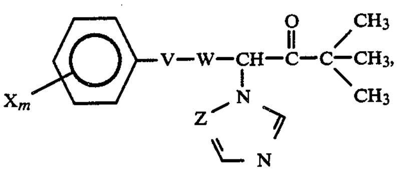

II and, if required, alkylation or acylation of the product.

Reduction with a complex hydride, preferably sodium borohydride, in a protic diluent, preferably methanol, ethanol or isopropanol, very predominantly gives the R*, R*-diastereomeric alcohols of the formula I, where $R^3$ and $R^4$ are each hydrogen. The diastereomeric triazolyl alcohols having a R*,S* configuration are predominantly obtained when a ketone of the formula II is reduced with (a) a secondary alcoholate, (b) an alkyl magnesium halide or (c) hydrogen in the presence of a suitable hyrogenation catalyst.

By way of explanation, it may be stated that compounds having two different chiral carbon atoms form four stereoisomers whose configurations can be named in accordance with the Cahn-Ingold-Prelog system (cf. for example D. Seebach and V. Prelog, Angew. Chem. 94, (1982), 696, and the literature cited therein). Two enantiomers having the configurations R,R and S,S constitute a diastereomer denoted by R*,R*, and the other diastereomer, denoted by R*,S*, is composed of the two enantiomers with the configurations R,S and S,R.

The alcohols of the formula I, where Y is CHOH, which are obtainable using the reducing agent (a), (b) or (c) contain a substantially larger amount of the R*,S* diastereomer than the R*,R* diastereomer, the amount of the latter in the mixture being, as a rule, well below 30%. Pure R*,S* diastereomers can be obtained therefrom simply by washing the crude products with a suitable solvent, eg. diisopropyl ether, or by recrystallization or other, conventional purifications steps, eg. chromatography.

For stereoselective reduction of the ketones of the formula II to give the R*,S* diastereomers of the formula I where Y is CHOH, the following procedure is adopted according to (a):

The ketone of the formula II (1 mole equivalent) is reacted with a secondary alcoholate, preferably with from 0.3 to 1.5 mole equivalents, and preferably an alcoholate of aluminum, eg. aluminum isopropylate, aluminum 2-butylate or aluminum cyclohexylate, in the presence of a diluent at from 60° to 160° C., preferably at the boiling point of the diluent. Suitable diluents are inert organic solvents, in particular alcohols, such as isopropanol or cyclohexanol. The resulting diastereomeric alcoholates are then hydrolyzed in a conventional manner with the aid of an acid to give the free alcohol of the formula I, where Y is CHOH.

For the stereoselective reduction in embodiment (b) of the above process, the ketone of the formula II (1 mole equivalent), is reacted with an alkyl magnesium halide which contains one or more $\beta$H atoms, preferably with from 0.7 to 1.5 mole equivalents, in the presence of a diluent at from 0° to 120° C. Examples of suitable alkyl magensium halides are ethyl magnesium chloride, isopropyl magnesium bromide, n-propyl magnesium bromide and isobutyl magnesium chloride. Preferred solvents for the reduction are ethers, such as diethyl ether, di-n-propyl ether, tetrahydrofuran or anisole, tertiary amines, such as N,N-diethylaniline, and phosphoric acid tris-(dimethylamide). The reaction is also preferably carried out in a mixture of these solvents with aliphatic or aromatic hydrocarbons, such as n-hexane or toluene. Depending on the solvent, the reaction temperature can be varied from 0° to 120° C., preferably from 30° to 100° C.

The magnesium alcoholates initially formed in this procedure are then converted to the alcohols by hydrolysis with water or a dilute aqueous acid, such as hydrochloric acid, sulfuric acid or preferably acetic acid, or particularly preferably with aqueous ammonium chloride solution, and, if desired, these alcohols are purified in a conventional manner by extraction, recrystallization or chromatography, after the aqueous phase has been removed.

For the stereoselective reduction in embodiment (c), the catalytic hydrogenation is most advantageously carried out over a noble metal catalyst. The metals of the platinum group are most suitable for this purpose. These metals can be precipitated onto inert carriers, a metal content of from 0.5 to 10% generally being sufficient. In certain circumstances, it may also be possible to use the pure metals, advantageously in finely divided form. A colloidal ruthenium oxide hydrate obtained by precipitation from an aqueous ruthenium trichloride solution at pH 8 has proven particularly useful. The oxide form is converted to the active catalyst under the reaction conditions.

The solvents used are preferably ethers, such as dioxane, tetrahydrofuran or glycol dimethyl ether.

The temperature can be varied within wide limits, temperatures of from 100° to 150° C. having proven particularly suitable. At these temperatures, superatmospheric pressure has to be employed, from 10 to 30 bar being sufficient. Higher pressures have an adverse effect on the selectivity.

The amount of catalyst is not critical and depends not only on the activity but also on the reaction temperature and the hydrogen partial pressure.

The alkylation or acylation to give the compounds of the formula I, where $R^3$ and $R^4$ are each H, is effected as described below for the compounds of the formula I where $R^3$ is H.

The azole compounds of the formula I as claimed in claim 1, in which $R^3$ is not hydrogen, are obtained by reacting a ketone of the formula

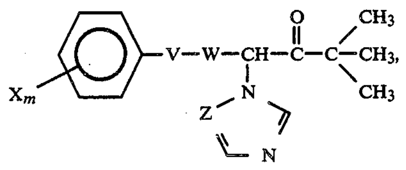

II where $X_m$, V, W and Z have the above meanings, with a Grignard compound of the formula $$R^3—MgHal \quad IV,$$

where $R^3$ is methyl, vinyl, allyl, ethynyl or propynyl and Hal is chlorine, bromine or iodine. In this reaction, from 0.8 to 2.4 equivalents of the Grignard compound are employed, and the procedure is preferably carried out in the presence of a solvent or diluent and in the presence or absence of a salt which increases the yield.

Preferred solvents are ethers, such as diethyl ether, di-n-propyl ether, tetrahydrofuran or anisole, tertiary amines, such as N,N-diethylaniline, and phosphoric acid tris-(dimethylamide). If necessary, the reaction can also be carried out in a mixture of these solvents with an aliphatic or aromatic hydrocarbon, such as n-hexane or toluene. Particularly suitable salts which increase the yield and suppress the usual side reactions are anhydrous magnesium halides, such as anhydrous magnesium bromide, and anhydrous tetraalkylammonium halides, eg. tetra-n-butylammonium chloride.

Depending on the solvent, the reaction temperatures can be varied from 0° to 100° C., temperatures from 0° to 60° C. being preferred. The magnesium alcoholates initially formed in this procedure are then converted to the alcohols by hydrolysis with water or a dilute aqueous acid, such as hydrochloric acid, sulfuric acid or, preferably, acetic acid, or particularly preferably with aqueous ammonium chloride solution, and, if desired, these alcohols are purified in a conventional manner by extraction, recrystallization or chromatography after the aqueous phase has been removed.

In the process for the preparation of the esters of the formula I where $R^4$ is $C_2$–$C_4$-alkanoyl, a secondary or tertiary alcohol of the formula I, where Y is $CR^3OR^4$ and $R^4$ is H, is reacted with an appropriate acyl chloride or anhydride in the presence of an acid acceptor, in the presence or absence of an aprotic solvent or diluent and preferably in the presence of an acylation catalyst, at from 0° to 100° C., preferably from 10° to 50° C. Inorganic bases, such as sodium amide, or particularly preferably pyridine can be employed as acid acceptors, in not less than equivalent amounts. Advantageously, imidazole or 4-dimethylaminopyridine is used as an acylation catalyst, in amounts of from 0.01 to 0.4 equivalent, unless pyridine is already present. Hydrocarbons, such as cyclohexane or toluene, esters, such as diethyl ether, or excess acid-binding amines, such as triethylamine or pyridine, can be used as solvents.

In the process for the preparation of the ethers of the formula I, where $R^4$ is $C_1$–$C_4$-alkyl, $C_2$–$C_4$-alkenyl or $C_2$–$C_4$-alkynyl, the tertiary alcohol of the formula I, where $R^4$ is H, or its alkali metal or quaternary ammonium salt, is reacted with an appropriate alkylating agent of the formula $$L—R^4 \qquad IV$$

in the presence or absence of a solvent or diluent, of an inorganic or organic base and of a reaction accelerator, at from 0° to 100° C.

Examples of the nucleophilically displaceable leaving groups L stated for the above process are halogen, preferably chlorine, bromine or iodine, alkylsulfate, preferably methylsulfate, unsubstituted or substituted alkylsulfonyloxy, preferably methanesulfonyloxy or trifluoromethanesulfonyloxy, or arylsulfonyloxy, preferably the tosylate radical.

Examples of suitable inorganic or organic bases, which, if required, may furthermore be used as acid acceptors in the reaction, are alkali metal and alkaline earth metal hydroxides, such as sodium hydroxide, potassium hydroxide or calcium hydroxide, alkali metal carbonates, such as potassium carbonate or sodium carbonate, alkali metal hydrides, such as sodium hydride, alkali metal or alkaline earth metal alcoholates, such as sodium methylate, magnesium methylate or sodium isopropylate, and tertiary amines, such as trimethylamine, triethylamine, N,N-dimethylaniline, N,N-dimethylcyclohexylamine, N-methylpiperidine or pyridine. Other conventional bases may also be used.

Using a suitable base, eg. an alkali metal hydride, such as sodium hydride, or lithium-alkyl, such as butyllithium, or an alkali metal or alkaline earth metal alcoholate, such as sodium methylate, the tertiary alcohols of the formula I, where $R^4$ is H, may also be first converted to the alcoholates in an upstream reaction and then introduced into the reaction in this form.

The preferred solvents and diluents include halohydrocarbons, eg. methylene chloride, chloroform, 1,2-dichloroethane or chlorobenzene, aliphatic and aromatic hydrocarbons, such as cyclohexane, petroleum ether, benzene, toluene or xylenes, esters, such as ethyl acetate, amides, such as dimethylformamide, nitriles, such as acetonitrile, sulfoxides, such as dimethyl sulfoxide, ketones, such as acetone or methyl ethyl ketone, and ethers, such as diethyl ether, tetrahydrofuran or dioxane, and mixtures of these.

Preferred reaction accelerators are metal halides, such as potassium iodide, crown ethers, quaternary ammonium compounds, such as tetrabutylammonium iodide, and acids, and combinations of these.

The reactions are generally carried out at from 0° to 100° C. over a period of from 1 to 60 hours, under atmospheric or superatmospheric pressure, continuously or batchwise.

The novel compounds are isolated by a conventional method. In general, the products obtained do not require any further purification but may be further purified by a conventional method such as recrystallization, extraction, distillation or chromatography.

The ketones of the formula II which are required as starting compounds for the preparation of the azoles of the formula I as claimed in claim 1 can be prepared by alkylating a known ketone of the formula V (German Laid-Open Application DOS No. 2,638,470) or its alkali metal enolate with an omega-aryloxyalkenyl or -alkynyl halide of the formula VI, in the presence or absence of a base and of a solvent or diluent.

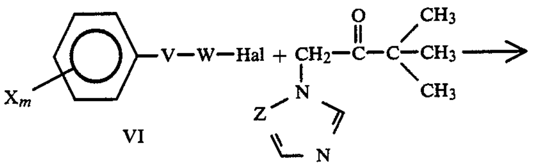

VI V

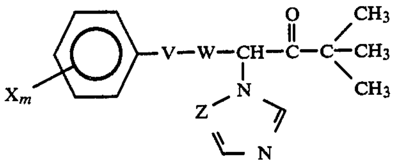

II

To do this, the ketone V can first be metalized to give an alkali metal enolate by reacting it, preferably in the presence of a polar aprotic solvent, such as dimethylformamide, acetonitrile or tetrahydrofuran, with from 0.8 to 1.2 equivalents, preferably 1.0 equivalent, of a metalizing reagent, such as sodium hydride, lithium diisopropylamide or n-butyl-lithium, at from 0° to 100° C., preferably from 10° to 50° C. From 0.8 to 2.0 equivalents, preferably 1.0 equivalent, of the particular omega-aryloxyalkenyl or alkynyl halide of the formula VI are then added, after which the ketone of the formula II is obtained at a reaction temperature of from 0° to 100° C., preferably from 5° to 30° C.

In one version of this process, a ketone V is reacted with an omega-aryloxyalkenyl or alkynyl halide VI in the presence of from 0.8 to 1.2 equivalents, preferably 1.0 equivalent, of a base, eg. potassium tert.-butoxide, sodium methoxide or potassium hydroxide, the reaction advantageously being carried out in the presence of a solvent or diluent at from 0° to 100° C. preferably from 5° to 50° C.

Suitable solvents or diluents are once again polar aprotic solvents, but alcohols, such as methanol or tert.-butanol, may also be used.

The omega-aryloxyalkenyl or -alkynyl halides VI are either known compounds or can readily be prepared by a conventional method, for example by monoalkylation of a phenol or a thiophenol with an unsaturated dihalohydrocarbon, eg. 1,4-dibromobut-2-ene or 1,4-dichlorobut-2-ene (cf. Houben-Weyl, Methoden der Organischen Chemie, Volume 6/3, pages 54–59, Thieme-Verlag, Stuttgart 1965).

If desired, the novel compounds of the formula I may also be converted to salts with inorganic or organic acids, for example to salts of hydrochloric acid, hydrobromic acid, nitric acid, oxalic acid, acetic acid, sulfuric acid, phosphoric acid or dodecylbenzenesulfonic acid. The activity of the salts is attributable to the cation, so that any anion can be chosen.

Furthermore, the compounds of the formula I can be converted to metal complexes by a conventional method. This can be effected by reacting these compounds with suitable metal salts, eg. copper(II) chloride, zinc(II) chloride, iron(III) chloride, copper(II) nitrate, manganese(II) chloride or nickel(II) bromide.

The Examples and methods which follow illustrate the preparation of the novel compounds of the formula I and of the intermediates.

METHOD 1

Preparation of trans-1,4-dibromobut-2-ene 500 ml (5.4 moles) of phosphorus tribromide were added dropwise, while cooling with ice, to 618 ml (7.5 moles) of cis-butene-1,4-diol dissolved in 1,000 ml of methylene chloride, the solution containing 5 ml of pyridine. When the exothermic reaction had died down, stirring was continued for 2 hours and the mixture was mixed with 1.5 l of ice water. The organic phase was separated off, washed once with sodium bicarbonate solution and three times with water, dried with sodium sulfate and freed from the solvent under reduced pressure. The dibromo compound was isomerized to the trans compound by stirring it with 0.5 g of iodine for 30 minutes at 150° C. Subsequent fractional distillation gave 1,540 g of trans-1,4-dibromobut-2-ene.

METHOD 2

Preparation of trans-1-(2-fluorophenoxy)-4-bromobut-2-ene 100 g (0.9 mole) of 2-fluorophenol and 477 g (2.7 moles) of trans-1,4-dibromobut-2-ene were stirred under reflux with 70 g of $K_2CO_3$ in 500 ml of acetone for 5 hours. The mixture was filtered, and acetone was evaporated off under reduced pressure, the residue was taken up in methylene chloride, the solution was washed four times with aqueous 1 N NaOH solution, and the methylene chloride phase was dried with sodium sulfate and freed from unreacted 1,4-dibromobutene under reduced pressure. 175 g of trans-1-(2-fluorophenoxy)-4-bromobut-2-ene remained.

EXAMPLE 1

Preparation of compound 4

Compound No. 4

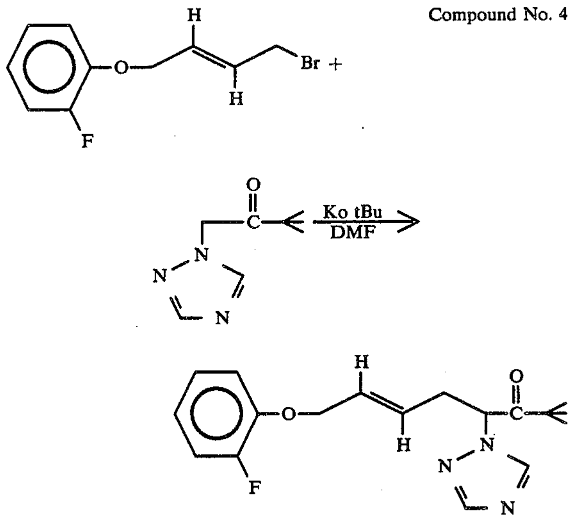

11.2 g (0.1 mole) of potassium tert.-butylate (KO t Bu) were added, a little at a time, to 15.7 g (0.09 mole) of triazolylpinacolone in 200 ml of dimethylformamide (DMF). After about 30 minutes, 23 g (0.09 mole) of trans-1-(2-fluorophenoxy)-4-bromobut-2-ene were added dropwise, and the mixture was stirred for 3 hours. After filtration, DMF was evaporated off, the residue was taken up in methylene chloride, and the solution was washed with water and dried with $NaSO_4$. The crude product obtained by evaporating off the solvent was purified by chromatography over silica gel, using methylene chloride as an eluant. 25 g of compound No. 4 were obtained as an oil.

EXAMPLE 2

Preparation of compound 5

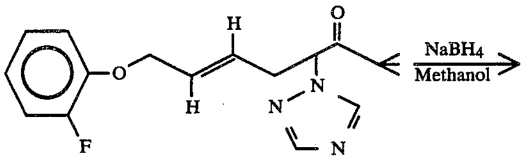

Compound No. 4

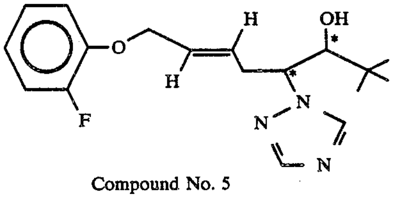

R*R* = Dia A

Compound No. 5

35 g (0.104 mole) of compound No. 4 in 200 ml of methanol were reduced by adding 4.1 g (0.104 mole) of sodium borohydride a little at a time. The mixture was stirred for 2 hours at about 20° C. and then evaporated down under reduced pressure, the residue was taken up in methylene chloride, the solution was extracted twice by shaking with water, dried over sodium sulfate and evaporated down, and, in this manner, 32 g of compound No. 5 were obtained as an oil, which was a diastereomer with a purity greater than 90% (Dia A=R*,R*-diastereomer).

EXAMPLE 3

Preparation of compound 6

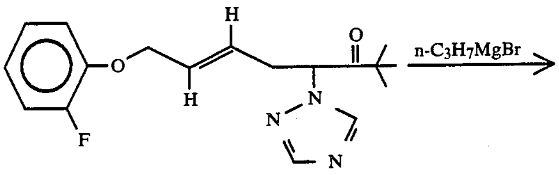

Compound No. 4

-continued

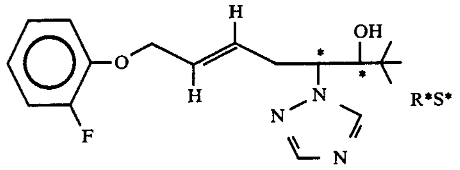

Compound No. 6

0.06 mole of n-propyl magnesium bromide was produced from n-propyl bromide and Mg in 50 ml of diethyl ether in a conventional manner. 10 g (0.03 mole) of compound No. 4, dissolved in 100 ml of toluene, were rapidly added dropwise. After 1 hour, 200 ml of aqueous ammonium chloride solution were added, the phases were separated, and the organic phase was dried with $Na_2SO_4$ and then freed from the solvent under reduced pressure. The product was crystallized with diisopropyl ether, and the crystals were filtered off under suction and dried to give 9 g of compound No. 6, which consisted of more than 90% of the R*,S*-diastereomer (=Dia B).

The compounds listed in the Table below can be prepared in a similar manner.

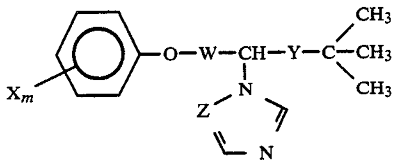

| Compound no. | $X_m$ | Z | W | Y | M.p. [°C.] |
|---|---|---|---|---|---|
| 1 | H | N | $CH_2$—CH=CH—$CH_2$ (trans) | C=O | 50–51 |
| 2 | H | N | $CH_2$—CH=CH—$CH_2$ (trans) | CHOH (Dia A) | oil |
| 3 | H | N | $CH_2$—CH=CH—$CH_2$ (trans) | CHOH (Dia B) | 126–128 |
| 4 | 2-F | N | $CH_2$—CH=CH—$CH_2$ (trans) | C=O | oil |
| 5 | 2-F | N | $CH_2$—CH=CH—$CH_2$ (trans) | CHOH (Dia A) | oil |
| 6 | 2-F | N | $CH_2$—CH=CH—$CH_2$ (trans) | CHOH (Dia B) | 74–76 |
| 7 | 3-F | N | $CH_2$—CH=CH—$CH_2$ (trans) | C=O | |
| 8 | 3-F | N | $CH_2$—CH=CH—$CH_2$ (trans) | CHOH (Dia A) | |
| 9 | 3-F | N | $CH_2$—CH=CH—$CH_2$ (trans) | CHOH (Dia B) | |
| 10 | 4-F | N | $CH_2$—CH=CH—$CH_2$ (trans) | C=O | |
| 11 | 4-F | N | $CH_2$—CH=CH—$CH_2$ (trans) | CHOH (Dia A) | |
| 12 | 4-F | N | $CH_2$—CH=CH—$CH_2$ (trans) | CHOH (Dia B) | |
| 13 | 2-$CH_3$ | N | $CH_2$—CH=CH—$CH_2$ (trans) | C=O | |
| 14 | 2-$CH_3$ | N | $CH_2$—CH=CH—$CH_2$ (trans) | CHOH (Dia A) | |
| 15 | 2-$CH_3$ | N | $CH_2$—CH=CH—$CH_2$ (trans) | CHOH (Dia B) | |
| 16 | 3-$CH_3$ | N | $CH_2$—CH=CH—$CH_2$ (trans) | C=O | |
| 17 | 3-$CH_3$ | N | $CH_2$—CH=CH—$CH_2$ (trans) | CHOH (Dia A) | |
| 18 | 3-$CH_3$ | N | $CH_2$—CH=CH—$CH_2$ (trans) | CHOH (Dia B) | |
| 19 | 4-$CH_3$ | N | $CH_2$—CH=CH—$CH_2$ (trans) | C=O | |
| 20 | 4-$CH_3$ | N | $CH_2$—CH=CH—$CH_2$ (trans) | CHOH (Dia A) | |
| 21 | 4-$CH_3$ | N | $CH_2$—CH=CH—$CH_2$ (trans) | CHOH (Dia B) | |
| 22 | 2-Cl | N | $CH_2$—CH=CH—$CH_2$ (trans) | C=O | |
| 23 | 2-Cl | N | $CH_2$—CH=CH—$CH_2$ (trans) | CHOH (Dia A) | |
| 24 | 2-Cl | N | $CH_2$—CH=CH—$CH_2$ (trans) | CHOH (Dia B) | |
| 25 | 3-Cl | N | $CH_2$—CH=CH—$CH_2$ (trans) | C=O | |
| 26 | 3-Cl | N | $CH_2$—CH=CH—$CH_2$ (trans) | CHOH (Dia A) | |
| 27 | 3-Cl | N | $CH_2$—CH=CH—$CH_2$ (trans) | CHOH (Dia B) | |
| 28 | 4-Cl | N | $CH_2$—CH=CH—$CH_2$ (trans) | C=O | |
| 29 | 4-Cl | N | $CH_2$—CH=CH—$CH_2$ (trans) | CHOH (Dia A) | |
| 30 | 4-Cl | N | $CH_2$—CH=CH—$CH_2$ (trans) | CHOH (Dia B) | |
| 31 | 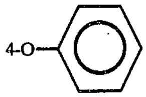 | N | $CH_2$—CH=CH—$CH_2$ (trans) | C=O | |

-continued

| | | | | | |
|---|---|---|---|---|---|
| 32 | 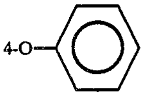 | N | $CH_2-CH=CH-CH_2$ (trans) | CHOH (Dia A) | |
| 33 | 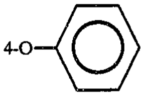 | N | $CH_2-CH=CH-CH_2$ (trans) | CHOH (Dia B) | |
| 34 | 4-O—$CH_3$ | N | $CH_2-CH=CH-CH_2$ (trans) | C=O | |
| 35 | 4-O—$CH_3$ | N | $CH_2-CH=CH-CH_2$ (trans) | CHOH (Dia A) | |
| 36 | 4-O—$CH_3$ | N | $CH_2-CH=CH-CH_2$ (trans) | CHOH (Dia B) | |
| 37 | 2-$CF_3$ | N | $CH_2-CH=CH-CH_2$ (trans) | C=O | |
| 38 | 2-$CF_3$ | N | $CH_2-CH=CH-CH_2$ (trans) | CHOH (Dia A) | |
| 39 | 2-$CF_3$ | N | $CH_2-CH=CH-CH_2$ (trans) | CHOH (Dia B) | |
| 40 | 3-$CF_3$ | N | $CH_2-CH=CH-CH_2$ (trans) | C=O | |
| 41 | 3-$CF_3$ | N | $CH_2-CH=CH-CH_2$ (trans) | CHOH (Dia A) | |
| 42 | 3-$CF_3$ | N | $CH_2-CH=CH-CH_2$ (trans) | CHOH (Dia B) | |
| 43 | 4-$CF_3$ | N | $CH_2-CH=CH-CH_2$ (trans) | C=O | |
| 44 | 4-$CF_3$ | N | $CH_2-CH=CH-CH_2$ (trans) | CHOH (Dia) | |
| 45 | 4-$CF_3$ | N | $CH_2-CH=CH-CH_2$ (trans) | CHOH (Dia B) | |
| 46 | 4-Br | N | $CH_2-CH=CH-CH_2$ (trans) | C=O | |
| 47 | 4-Br | N | $CH_2-CH=CH-CH_2$ (trans) | CHOH (Dia A) | |
| 48 | 4-Br | N | $CH_2-CH=CH-CH_2$ (trans) | CHOH (Dia B) | |
| 49 | 4-tBu | N | $CH_2-CH=CH-CH_2$ (trans) | CHOH (Dia B) | |
| 50 | H | N | $CH_2-C\equiv C-CH_2$ | C=O | oil |
| 51 | H | N | $CH_2-C\equiv C-CH_2$ | CHOH (Dia A) | 74–75 |
| 52 | H | N | $CH_2-C\equiv C-CH_2$ | CHOH (Dia B) | |
| 53 | 2-F | N | $CH_2-C\equiv C-CH_2$ | C=O | |
| 54 | 2-F | N | $CH_2-C\equiv C-CH_2$ | CHOH (Dia A) | |
| 55 | 2-F | N | $CH_2-C\equiv C-CH_2$ | CHOH (Dia B) | |
| 56 | 3-F | N | $CH_2-C\equiv C-CH_2$ | C=O | |
| 57 | 3-F | N | $CH_2-C\equiv C-CH_2$ | CHOH (Dia A) | |
| 58 | 3-F | N | $CH_2-C\equiv C-CH_2$ | CHOH (Dia B) | |
| 59 | 4-F | N | $CH_2-C\equiv C-CH_2$ | C=O | oil |
| 60 | 4-F | N | $CH_2-C\equiv C-CH_2$ | CHOH (Dia A) | |
| 61 | 4-F | N | $CH_2-C\equiv C-CH_2$ | CHOH (Dia B) | |
| 62 | $2CH_3$ | N | $CH_2-C\equiv C-CH_2$ | C=O | |
| 63 | 2-$CH_3$ | N | $CH_2-C\equiv C-CH_2$ | CHOH (Dia A) | |
| 64 | 2-$CH_3$ | N | $CH_2-C\equiv C-CH_2$ | CHOH (Dia B) | |
| 65 | 3-$CH_3$ | N | $CH_2-C\equiv C-CH_2$ | C=O | |
| 66 | 3-$CH_3$ | N | $CH_2-C\equiv C-CH_2$ | CHOH (Dia A) | |
| 67 | 3-$CH_3$ | N | $CH_2-C\equiv C-CH_2$ | CHOH (Dia B) | |
| 68 | 4-$CH_3$ | N | $CH_2-C\equiv C-CH_2$ | C=O | oil |
| 69 | 4-$CH_3$ | N | $CH_2-C\equiv C-CH_2$ | CHOH (Dia A) | |
| 70 | 4-$CH_3$ | N | $CH_2-C\equiv C-CH_2$ | CHOH (Dia B) | oil |
| 71 | 2-Cl | N | $CH_2-C\equiv C-CH_2$ | C=O | |
| 72 | 2-Cl | N | $CH_2-C\equiv C-CH_2$ | CHOH (Dia A) | |
| 73 | 2-Cl | N | $CH_2-C\equiv C-CH_2$ | CHOH (Dia B) | |
| 74 | 3-Cl | N | $CH_2-C\equiv C-CH_2$ | C=O | oil |
| 75 | 3-Cl | N | $CH_2-C\equiv C-CH_2$ | CHOH (Dia A) | |
| 76 | 3-Cl | N | $CH_2-C\equiv C-CH_2$ | CHOH (Dia B) | oil |
| 77 | 4-Cl | N | $CH_2-C\equiv C-CH_2$ | C=O | |
| 78 | 4-Cl | N | $CH_2-C\equiv C-CH_2$ | CHOH (Dia A) | |
| 79 | 4-Cl | N | $CH_2-C\equiv C-CH_2$ | CHOH (Dia B) | |
| 80 | 2,4-$Cl_2$ | N | $CH_2-C\equiv C-CH_2$ | C=O | oil |
| 81 | 2,4-$Cl_2$ | N | $CH_2-C\equiv C-CH_2$ | CHOH (Dia A) | |
| 82 | 2,4-$Cl_2$ | N | $CH_2-C\equiv C-CH_2$ | CHOH (Dia B) | oil |
| 83 | 2,4,6-$Cl_3$ | N | $CH_2-C\equiv C-CH_2$ | C=O | |
| 84 | 2,4,6-$Cl_3$ | N | $CH_2-C\equiv C-CH_2$ | CHOH (Dia A) | |
| 85 | 2,4,6-$Cl_3$ | N | $CH_2-C\equiv C-H_2$ | CHOH (Dia B) | |
| 86 | H | H | $-CH_2-CH=C(CH_3)CH_2-$ (trans) | C=O | |
| 87 | H | N | $-CH_2-CH=C(CH_3)CH_2-$ (trans) | CHOH (Dia A) | |
| 88 | H | N | $-CH_2-CH=C(CH_3)CH_2-$ (trans) | CHOH (Dia B) | |
| 89 | H | N | $-CH_2CCl=CClCH_2-$ (trans) | C=O | |
| 90 | H | N | $-CH_2CCl=CClCH_2-$ (trans) | CHOH (Dia A) | |
| 91 | H | N | $-CH_2CCl=CClCH_2-$ (trans) | CHOH (Dia B) | |
| 92 | 2-F | N | $-CH_2CH=C(CH_3)CH_2-$ (trans) | C=O | |
| 93 | 2-F | N | $-CH_2CH=C(CH_3)CH_2-$ (trans) | CHOH (Dia A) | |
| 94 | 2-F | N | $-CH_2CH=C(CH_3)CH_2-$ (trans) | CHOH (Dia B) | |
| 95 | 2-F | N | $-CH_2CCl=CClCH_2-$ (trans) | C=O | |
| 96 | 2-F | N | $-CH_2CCl=CClCH_2-$ (trans) | CHOH (Dia A) | |
| 97 | 2-F | N | $-CH_2CCl=CClH_2-$ (trans) | CHOH (Dia B) | |
| 98 | 4-F | N | $-CH_2CCl=CClCH_2-$ (trans) | C=O | |
| 99 | 4-F | N | $-CH_2CCl=CClCH_2-$ (trans) | CHOH (Dia A) | |
| 100 | 4-F | N | $-CH_2CCl=CClCH_2-$ (trans) | CHOH (Dia B) | |
| 101 | 4-F | N | $-CH_2C(CH_3)=C(CH_3)CH_2-$ (trans) | C=O | |
| 102 | 4-F | N | $-CH_2C(CH_3)=C(CH_3)CH_2-$ (trans) | CHOH (Dia A) | |
| 103 | 4-F | N | $-CH_2C(CH_3)=C(CH_3)CH_2-$ (trans) | CHOH (Dia B) | |

-continued

| | | | | | |
|---|---|---|---|---|---|
| 104 | H | CH | $-CH_2CH{=}CHCH_2-$ (trans) | C=O | |
| 105 | H | CH | $-CH_2CH{=}CHCH_2-$ (trans) | CHOH (Dia A) | |
| 106 | H | CH | $-CH_2CH{=}CHCH_2-$ (trans) | CHOH (Dia B) | |
| 107 | 2-F | CH | $-CH_2CH{=}CHCH_2-$ (trans) | C=O | |
| 108 | 2-F | CH | $CH_2-CH{=}CH-CH_2$ (trans) | CHOH (Dia A) | |
| 109 | 2-F | CH | $CH_2-CH{=}CH-CH_2$ (trans) | CHOH (Dia B) | |
| 110 | 2-Cl | CH | $CH_2-CH{=}CH-CH_2$ (trans) | C=O | |
| 111 | 2-Cl | CH | $CH_2-CH{=}CH-CH_2$ (trans) | CHOH (Dia A) | |
| 112 | 2-Cl | CH | $CH_2-CH{=}CH-CH_2$ (trans) | CHOH (Dia B) | |
| 113 | 4-Cl | CH | $CH_2-CH{=}CH-CH_2$ (trans) | C=O | |
| 114 | 4-Cl | CH | $CH_2-CH{=}CH-CH_2$ (trans) | CHOH (Dia A) | |
| 115 | 4-Cl | CH | $CH_2-CH{=}CH-CH_2$ (trans) | CHOH (Dia B) | |
| 116 | 2-Cl | N | $CH_2CH{=}CHCH_2$ cis/trans mixture | C=O | oil |
| 117 | 2-Cl | N | $CH_2CH{=}CHCH_2$ cis/trans mixture | CHOH (Dia A) | oil |
| 118 | 2-Cl | N | $CH_2CH{=}CHCH_2$ cis/trans mixture | CHOH (Dia B) | |
| 119 | 3-Cl | N | $CH_2CH{=}CH-CH_2$ cis/trans mixture | C=O | oil |
| 120 | 3-Cl | N | $CH_2CH{=}CHCH_2$ cis/trans mixture | CHOH (Dia A) | oil |
| 121 | 3-Cl | N | $CH_2CH{=}CHCH_2$ cis/trans mixture | CHOH (Dia B) | |
| 122 | 4-Cl | N | $CH_2CH{=}CHCH_2$ cis/trans mixture | C=O | |
| 123 | 4-Cl | N | $CH_2CH{=}CHCH_2$ cis/trans mixture | CHOH (Dia A) | oil |
| 124 | 4-Cl | N | $CH_2CH{=}CHCH_2$ cis/trans mixture | CHOH (Dia B) | |
| 125 | 2-$CH_3$ | N | $CH_2CH{=}CHCH_2$ cis/trans mixture | C=O | oil |
| 126 | 2-$CH_3$ | N | $CH_2CH{=}CHCH_2$ cis/trans mixture | CHOH (Dia A) | oil |
| 127 | 2-$CH_3$ | N | $CH_2CH{=}CHCH_2$ cis/trans mixture | CHOH (Dia B) | |
| 128 | 3-$CH_3$ | N | $CH_2CH{=}CHCH_2$ cis/trans mixture | C=O | oil |
| 129 | 3-$CH_3$ | N | $CH_2CH{=}CHCH_2$ cis/trans mixture | CHOH (Dia A) | oil |
| 130 | 3-$CH_3$ | N | $CH_2CH{=}CHCH_2$ cis/trans mixture | CHOH (Dia B) | |
| 131 | 4-$CH_3$ | N | $CH_2CH{=}CHCH_2$ cis/trans mixture | C=O | oil |
| 132 | 4-$CH_3$ | N | $CH_2CH{=}CHCH_2$ cis/trans mixture | CHOH (Dia A) | oil |
| 133 | 4-$CH_3$ | N | $CH_2CH{=}CHCH_2$ cis/trans mixture | CHOH (Dia B) | |
| 134 | 4-O 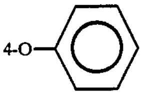 | N | $CH_2CH{=}CHCH_2$ cis/trans mixture | C=O | oil |
| 135 | 4-O 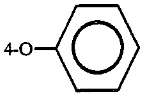 | N | $CH_2CH{=}CHCH_2$ cis/trans mixture | CHOH (Dia A) | oil |
| 136 | 4-O 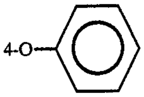 | N | $CH_2CH{=}CHCH_2$ cis/trans mixture | CHOH (Dia B) | |
| 137 | H | N | $CH_2-CH{=}CH-CH_2$ (trans) | C=O | |
| 138 | H | H | $CH_2-CH{=}CH-CH_2$ (trans) | CHOH (Dia A) | |
| 139 | H | N | $CH_2-CH{=}CH-CH_2$ (trans) | CHOH (Dia B) | |
| 140 | 2-F | N | $CH_2-CH{=}CH-CH_2$ (trans) | C=O | |
| 141 | 2-F | N | $CH_2-CH{=}CH-CH_2$ (trans) | CHOH (Dia A) | |
| 142 | 2-F | N | $CH_2-CH{=}CH-CH_2$ (trans) | CHOH (Dia B) | |
| 143 | 2-$CH_3$ | N | $CH_2-CH{=}CH-CH_2$ (trans) | C=O | |
| 144 | 2-$CH_3$ | N | $CH_2-CH{=}CH-CH_2$ (trans) | CHOH (Dia A) | |
| 145 | 2-$CH_3$ | N | $CH_2-CH{=}CH-CH_2$ (trans) | CHOH (Dia B) | |
| 146 | 2-Cl | N | $CH_2-CH{=}CH-CH_2$ (trans) | C=O | |
| 147 | 2-Cl | N | $CH_2-CH{=}CH-CH_2$ (trans) | CHOH (Dia A) | |
| 148 | 2-Cl | N | $CH_2-CH{=}CH-CH_2$ (trans) | CHOH (Dia B) | |
| 149 | 3-Cl | N | $CH_2-CH{=}CH-CH_2$ (trans) | C=O | |
| 150 | 3-Cl | N | $CH_2-CH{=}CH-CH_2$ (trans) | CHOH (Dia A) | |
| 151 | 3-Cl | N | $CH_2-CH{=}CH-CH_2$ (trans) | CHOH (Dia B) | |
| 152 | 3-$CF_3$ | N | $CH_2-CH{=}CH-CH_2$ (trans) | C=O | |
| 153 | 3-$CF_3$ | N | $CH_2-CH{=}CH-CH_2$ (trans) | CHOH (Dia A) | |
| 154 | 3-$CF_3$ | N | $CH_2-CH{=}CH-CH_2$ (trans) | CHOH (Dia B) | |
| 155 | 4-F | N | $CH_2-CH{=}CH-CH_2$ (trans) | C=O | |
| 156 | 4-F | N | $CH_2-CH{=}CH-CH_2$ (trans) | CHOH (Dia A) | |
| 157 | 4-F | N | $CH_2-CH{=}CH-CH_2$ (trans) | CHOH (Dia B) | |
| 158 | 4-Cl | N | $CH_2-CH{=}CH-CH_2$ (trans) | C=O | |
| 159 | 4-Cl | N | $CH_2-CH{=}CH-CH_2$ (trans) | CHOH (Dia A) | |
| 160 | 4-Cl | N | $CH_2-CH{=}CH-CH_2$ (trans) | CHOH (Dia B) | |
| 161 | H | CH | $CH_2-CH{=}CH-CH_2$ (trans) | C=O | |
| 162 | H | CH | $CH_2-CH{=}CH-CH_2$ (trans) | CHOH (Dia A) | |
| 163 | H | CH | $CH_2-CH{=}CH-CH_2$ (trans) | CHOH (Dia B) | |
| 164 | 4-F | CH | $CH_2-CH{=}CH-CH_2$ (trans) | C=O | |
| 165 | 4-F | CH | $CH_2-CH{=}CH-CH_2$ (trans) | CHOH (Dia A) | |
| 166 | 4-F | CH | $CH_2-CH{=}CH-CH_2$ (trans) | CHOH (Dia B) | |

-continued

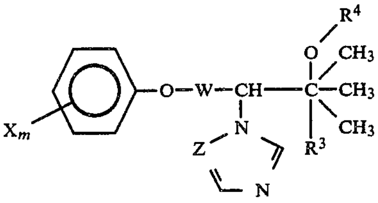

| Compound no. | $X_m$ | Z | W | $R^4$ | $R^3$ | M.p. [°C.] |
|---|---|---|---|---|---|---|
| 167 | H | N | $CH_2-CH=CH-CH_2$ (trans) | H | $-CH_3$ | |
| 168 | H | N | $CH_2-CH=CH-CH_2$ (trans) | H | $-CH=CH_2$ | |
| 169 | H | N | $CH_2-CH=CH-CH_2$ (trans) | H | $-C\equiv CH$ | |
| 170 | H | N | $CH_2-CH=CH-CH_2$ (trans) | H | $-C\equiv C-CH_3$ | |
| 171 | H | N | $CH_2-CH=CH-CH_2$ (trans) | H | $-CH_2-CH=CH_2$ | |
| 172 | H | CH | $CH_2-CH=CH-CH_2$ (trans) | H | $-CH_3$ | |
| 173 | H | CH | $CH_2-CH=CH-CH_2$ (trans) | H | $-CH=CH_2$ | |
| 174 | H | CH | $CH_2-CH=CH-CH_2$ (trans) | H | $-C\equiv CH$ | |
| 175 | H | H | $CH_2-CH=CH-CH_2$ (trans) | H | $-C\equiv C-CH_3$ | |
| 176 | H | CH | $CH_2-CH=CH-CH_2$ (trans) | H | $-CH_2-HC=CH_2$ | |
| 177 | H | N | $CH_2-CH=CH-CH_2$ (trans) | $CH_3$ | $CH_3$ | |
| 178 | H | N | $CH_2-CH=CH-CH_2$ (trans) | $CH_2-CH=CH_2$ | $CH_3$ | |
| 179 | 2-F | N | $CH_2-CH=CH-CH_2$ (trans) | H | $-CH_3$ | |
| 180 | 2-F | N | $CH_2-CH=CH-CH_2$ (trans) | H | $-CH=CH_2$ | |
| 181 | 2-F | N | $CH_2-CH=CH-CH_2$ (trans) | H | $-C\equiv C-CH_3$ | |
| 182 | 2-F | N | $CH_2-CH=CH-CH_2$ (trans) | H | $-CH_2-CH=CH_2$ | |
| 183 | 2-F | N | $CH_2-CH=CH-CH_2$ (trans) | $CH_3$ | $CH_3$ | |
| 184 | 2-F | N | $CH_2-CH=CH-CH_2$ (trans) | $CH_2-C=CH_2$ | $CH_3$ | |
| 185 | H | N | $CH_2-CH=CH-CH_2$ (trans) | $CH_3$ | H | |

Footnote
Dia A: denotes preferentially (>85%) or exclusively diastereomer A with R*,R*-configuration
Dia B: denotes preferentially (>85%) or exclusively diastereomer B with R*,S*-configuration
By "cis/trans mixture" is meant a mixture of double-bond isomers consisting of 40-60% of the one, and correspondingly 60-40% of the other isomer.

The novel compounds are used as fungicides by spraying or dusting the plants with the active ingredients, or treating the seed of plants with the active ingredients. Application may be effected before or after infection of the plants or seed by the fungi.

The compounds according to the invention may be converted into the usual formulations, e.g. solutions, emulsions, suspensions, dusts, powders, pastes and granules. The forms of application depend entirely on the purpose for which the agents are being used; they should at all events ensure a fine and uniform distribution of the active ingredient. The formulations are prepared in conventional manner, e.g., by extending the active ingredient with solvents and/or carriers, if desired using emulsifiers and dispersants. Where water is used as diluent, other organic solvents may also be employed as auxiliary solvents. Suitable compounds for preparing such formulations are solvents such as aromatics (e.g., xylene, benzene), chlorinated aromatics (e.g., chlorobenzenes), paraffins (e.g., petroleum fractions), alcohols (e.g., methanol, butanol), amines (e.g., ethanolamine, dimethylformamide), and water; carriers such as natural rock flours (e.g., kaolins, diatomaceous earth, talc, chalk) and synthetic rock flours (e.g., highly disperse silicic acid, silicates); emulsifiers such as nonionic and anionic emulsifying agents (e.g. polyoxyethylene-fatty alcohol ethers, alkyl sulfonates and aryl sulfonates); and dispersants such as lignin, sulfite waste liquors and methyl cellulose.

The formulations generally contain from 0.1 to 95, and preferably from 0.5 to 90, wt% of active ingredient.

The application rates depend on the effect desired, and range from 0.02 to 3 kg of active ingredient per hectare, or more. The novel compounds may also be used for protecting materials, e.g., for combatting wood-destroying fungi such as *Coniophora puteana* and *Polystictus versicolor.* The novel active ingredients may also be employed as fungicidally effective components of oily wood preservatives for protecting wood against wood-discoloring fungi. The agents are applied by treating, e.g., impregnating or painting, the wood with them.

The formulations and the ready-to-use products made therefrom, e.g., solutions, emulsions, suspensions, powders, dusts, pastes or granules, are applied in known manner, for example by spraying, atomizing, dusting, scattering, seed-disinfecting, or watering.

Examples of such formulations are given below.

I. 90 parts by weight of Compound no. 1 is mixed with 10 parts by weight of N-methyl-alpha-pyrrolidone. A mixture is obtained which is suitable for application in the form of very fine drops.

II. 20 parts by weight of Compound no. 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of Compound no. 3 is dissolved in a mixture consisting of 40 parts by weight of cyclohexanone, 30 parts by weight of isobutanol, and 20 parts by weight of the adduct of 40 moles of ethylene oxide and 1 mole of castor oil. By pouring the solution into water and finely distributing it therein, an aqueous dispersion is obtained.

IV. 20 parts by weight of Compound no. 6 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of Compound no. 1 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of Compound no. 2 is intimately mixed with 97 parts by weight of particulate kaolin. A dust is obtained containing 3% by weight of the active ingredient.

VII. 30 parts by weight of Compound no. 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of Compound no. 3 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts of Compound no. 6 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

In these application forms, the agents according to the invention may also be mixed and applied with other active ingredients, e.g., herbicides, insecticides, growth regulators, other fungicides, and fertilizers. When mixed with other fungicides, the spectrum of fungicidal action is in many cases increased.

The following list of fungicides with which the active ingredients according to the invention may be combined is intended to illustrate, and not restrict, the combination possibilities:

sulfur
dithiocarbamates and derivatives thereof, such as
ferric dimethyldithiocarbamate
zinc dimethyldithiocarbamate
zinc ethylenebisthiocarbamate
manganese ethylenebisdithiocarbamate
tetramethylthiuram disulfide
manganese-zinc ethylenediamine-bisdithiocarbamate
ammonia complex of zinc-(N,N'-ethylene)-bisdithiocarbamate and
N,N'-polyethylene-bis-(thiocarbamoyl)-disulfide ammonia complex of zinc-(N,N'-propylene-bisdithiocarbamate) and
N,N'-polypropylene-bis-(thiocarbamoyl)-disulfide nitro derivatives, such as
dinitro-(1-methylheptyl)-phenylcrotonate
2-sec-butyl-4,6-dinitrophenyl-3,5-dimethylacrylate
2-sec-butyl-4,6-dinitrophenylisopropylcarbonate
diisopropyl 5-nitroisophthalate heterocyclic structures, such as
2-heptadecyl-2-imidazoline acetate
2,4-dichloro-6-(o-chloroanilino)-s-triazine
O,O-diethylphthalimidophosphorothionate
5-amino-1-[bis-(dimethylamino)-phosphynyl]-3-phenyl-1,2,4-triazole
2,3-dicyano-1,4-dithiaanthraquinone
2-thio-1,3-dithio-(4,5-b)-quinoxaline
methyl 1-(butylcarbamoyl)-2-benzimidazole carbamate
2-methoxycarbonylaminobenzimidazole
2-[furyl-(2)]-benzimidazole
2-[thiazolyl-(4)]-benzimidazole
N-(1,1,2,2-tetrachloroethylthio)-tetrahydrophthalimide
N-trichloromethylthiotetrahydrophthalimide
N-trichloromethylphthalimide
N-dichlorofluoromethylthio-N',N'-dimethyl-N-phenyl-sulfuric acid diamide
5-ethoxy-3-trichloromethyl-1,2,3-thiadiazole
2-thiocyanomethylthiobenzthiazole
1,4-dichloro-2,5-dimethoxybenzene
4-(2-chlorophenylhydrazono)-3-methyl-5-isoxazolone
pyridine-2-thio-1-oxide
8-hydroxyquinoline and its copper salt
2,3-dihydro-5-carboxanilido-6-methyl-1,4-oxathiyne-4,4-dioxide
2,3-dihydro5-carboxanilido-6-methyl-1,4-oxathiyne
2-methyl-5,6-dihydro-4-H-pyran-3-carboxanilide
2-methyl-furan-3-carboxanilide
2,5-dimethyl-furan-3-carboxanilide
2,4,5-trimethyl-furan-3-carboxanilide
2,5-dimethyl-furan-3-carboxylic acid cyclohexylamide
N-cyclohexyl-N-methoxy-2,5-dimethyl-furan-3-carboxamide
2-methyl-benzoic acid anilide
2-iodobenzoic acid anilide
N-formyl-N-morpholine-2,2,2-trichloroethylacetal
piperazine-1,4-diylbis-(1-(2,2,2-trichloroethyl)-formamide
1-(3,4-dichloroanilino)-1-formylamino-2,2,2-trichloroethane
2,6-dimethyl-N-tridecyl-morpholine and its salts
2,6-dimethyl-N-cyclododecyl-morpholine and its salts
N-[3-(p-tert.-butylphenyl)-2-methylpropyl]-cis-2,6-dimethylmorpholine
N-[3-(p-tert.-butylphenyl)-2-methylpropyl]-piperidine
1-[2-(2,4-dichlorophenyl)-4-ethyl-1,3-dioxolan-2-yl-ethyl]-1-H-1,2,4-triazole
1-[2-(2,4-dichlorophenyl)-4-n-propyl-1,3-dioxolan-2-yl-ethyl]-1-H-1,2,4-triazole
N-(n-propyl)-N-(2,4,6-trichlorophenoxyethyl)-N'-imidazol-ylurea
1-(4-chlorophenoxy)-3,3-dimethyl-1-(1H-1,2,4-triazol-1-yl)-2-butanone
1-(4-chlorophenoxy)-3,3-dimethyl-1-(1H-1,2,4-triazol-1-yl)-2-butanol
alpha-(2-chlorophenyl)-alpha-(4-chlorophenyl)-5-pyrimidinemethanol
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene
1,2-bis-(3-methoxycarbonyl)-2-thioureido)-benzene and various fungicides, such as
dodecylguanidine acetate
3-[2-(3,5-dimethyl-2-oxycyclohexyl)-2-hydroxyethyl]-glutarimide
hexachlorobenzene
D,L-methyl-N-(2,6-dimethylphenyl)-N-(2-furoyl)-alanate
methyl D,L-N-(2,6-dimethylphenyl)-N-(2-methoxyacetyl)-alanate N-(2,6-dimethylphenyl)-N-chloroacetyl-D,L-2-aminobutyrolactone
methyl DL-N-(2,6-dimethylphenyl)-N-(phenylacetyl)-alanate
5-methyl-5-vinyl-3-(3,5-dichlorophenyl)-2,4-dioxo-1,3-oxazolidine
3-(3,5-dichlorophenyl)-5-methyl-5-methoxymethyl-1,3-oxazolidine-2,4-dione
3-(3,5-dichlorophenyl)-1-isopropyl-carbamoylhydantoin
N-(3,5-dichlorophenyl)-1,2-dimethyl-cyclopropane-1,2-dicarboximide
2-cyano-N-(ethylaminocarbonyl)-2-(methoximino)-acetamide
1-(2-(2,4-dichlorophenyl)-pentyl)-1H-1,2,4-triazole
2,4-difluoro-alpha-(1H-1,2,4-triazol-1-yl-methyl)-benzhydryl alcohol.

The active ingredients according to the invention and their salts and metal complex compounds have an excellent action on a wide spectrum of plant-pathogenic fungi, especially from the Ascomycetes, Basidiomycetes and Deuteromycetes classes. Some of them have a systemic action and may be used as soil or foliar fungicides.

The fungicidal compounds are of particular interest for combatting a large number of fungi in various crops or their seed, especially wheat, rye, barley, oats, rice, Indian corn, cotton, soybeans, coffee, sugarcane, fruit, ornamentals in horticulture, and vegetables, such as cucumbers, beans and Cucurbitaceae.

The novel compounds are particularly suitable for combatting the following diseases: *Erysiphe graminis* in cereals, *Erysiphe cichoriacearum* in Cucurbitaceae, *Podosphaera leucotricha* in apples, *Uncinula necator* in grapes, Puccinia species in cereals, *Rhizoctonia solani* in cotton, Ustilago species in cereals and sugarcane, *Venturia inaequalis* (scab) in apples, Septoria nodorum in wheat, *Botrytis cinerea* in strawberries and grapes, *Cercospora musae* in bananas, *Pseudocercosporella herpotrichloides* in wheat and barley, *Pyricularia oryzae* in rice, *Hemileia vastatrix* in coffee, *Alternaria solani* in potatoes and tomatoes, Verticillium in cotton and vegetables, and Peronospora in grapes.

The novel compounds are particularly effective on Botrytis and Alternaria.

The fungicidal action is demonstrated by the following experiments. The prior art compound 1-[2-(2,4-dichlorophenyl)-2-(2-propenyloxy)-ethyl]-1H-imidazole (A) was used for comparison purposes.

EXPERIMENT 1

Action on wheat mildew

Leaves of pot-grown wheat seedlings of the "Jubilar" variety were sprayed with aqueous liquors, the solids of which consisted of 80% (by weight) of active ingredient and 20% of emulsifier, and dusted, 24 hours after the sprayed-on layer had dried, with spores of wheat mildew (*Erysiphe graminis* var. *tritici*). The plants were then placed in a greenhouse at 20° to 22° C. and 75 to 80% relative humidity. The extent of mildew spread was determined after 7 days.

The results of the experiment show that novel active ingredients 3 and 6, applied as 0.025% spray liquors, had a better fungicidal action (e.g., 100%) than prior art active ingredient A (97%).

EXPERIMENT 2

Action on leaf rust of wheat

Leaves of pot-grown wheat seedlings of the "Jubilar" variety were dusted with spores of rust (*Puccinia recondita*). The pots were then placed in a high humidity (90–95%) chamber at from 20° to 22° C. for 24 hours. During this time, the spores germinated and the germ tubes penetrated into the leaf tissue. The infected plants were then sprayed to run-off with aqueous liquors, the solids comprising 80% of active ingredient and 20% of emulsifier. After the spray coating had dried, the test plants were set up in a greenhouse at from 20° to 22° C. and from 65 to 70% relative humidity. After 8 days, the degree of development of the rust fungi on the leaves was determined.

The results of this experiment show that novel active ingredients 1, 2, 3 and 6, applied as 0.025% spray liquors, had a better fungicidal action (e.g., 100%) than prior art active ingredient A (e.g., 70%).

EXPERIMENT 3

Action on *Botrytis cinerea* in pimientos

Pimiento seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus *Botrytis cinerea,* and placed at 22° to 24° C. in a chamber of high humidity. After 5 days, the disease had spread to such a great extent on the untreated plants that the necroses covered the major portion of the leaves.

The results of this experiment show that novel active ingredients 1, 2, 3 and 6, applied as 0.05% spray liquors, had a better fungicidal action (e.g., 97%) than prior art active ingredient A (e.g., 70%).

We claim:

1. An azole compound of the formula

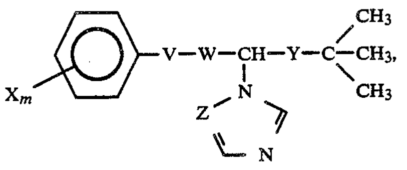

(I)

where V is oxygen or sulfur, X is hydrogen, fluorine, chlorine, bromine, $C_1$–$C_4$-alkyl, $C_1$–$C_4$-alkoxy, trifluoromethyl, phenyl or phenoxy, m is an integer from 1 to 5, the individual atoms or groups being identical or different when m is greater than 1, W is a group of the formula $(CH_2)_v—CR^1{=}CR^2—(CH_2)_t$, where $R^1$ and $R^2$ are identical or different and are each hydrogen, methyl, ethyl, chlorine or fluorine, or is a group of the formula $(CH_2)_v—C{\equiv}C—(CH_2)_t$, and v and t are identical or different and are each 1, 2 or 3, Z is CH or N, and Y is C=O or $CR^3OR^4$, where $R^3$ is hydrogen, methyl, vinyl, allyl, ethynyl or propynyl, and $R^4$ is hydrogen, $C_1$–$C_4$-alkyl, $C_2$–$C_4$-alkenyl, $C_2$–$C_4$-alkynyl or $C_2$–$C_4$-alkanoyl, and its plant-tolerated addition salts with acids and metal complexes.

2. A fungicidal composition containing an inert additive and an azole compound of the formula

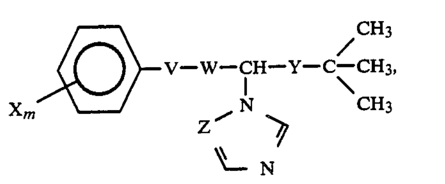

(I)

where V is oxygen or sulfur, X is hydrogen, fluorine, chlorine, bromine, $C_1$-$C_4$-alkyl, $C_1$-$C_4$-alkoxy, trifluoromethyl, phenyl or phenoxy, m is an integer from 1 to 5, the individual atoms or groups being identical or different when m is greater than 1, W is a group of the formula $(CH_2)_v$—$CR^1$=$CR^2$—$(CH_2)_t$, where $R^1$ and $R^2$ are identical or different and are each hydrogen, methyl, ethyl, chlorine or fluorine, or is a group of the formula $(CH_2)_v$—C≡C—$(CH_2)_t$, and v and t are identical or different and are each 1, 2 or 3, Z is CH or N, and Y is C=O or $CR^3OR^4$, where $R^3$ is hydrogen, methyl, vinyl, allyl, ethynyl or propynyl, and $R^4$ is hydrogen, $C_1$-$C_4$-alkyl, $C_2$-$C_4$-alkenyl, $C_2$-$C_4$-alkynyl or $C_2$-$C_4$-alkanoyl, or a plant-tolerated acid addition salt or metal complex thereof.

3. A process for combatting fungi, wherein the fungi or the materials, areas, plants or seed threatened by fungus attack are treated with a fungicidally effective amount of an azole compound of the formula

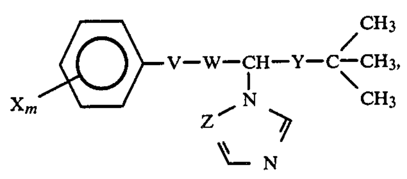

(I)

where V is oxygen or sulfur, X is hydrogen, fluorine, chlorine, bromine, $C_1$-$C_4$-alkyl, $C_1$-$C_4$-alkoxy, trifluoromethyl, phenyl or phenoxy, m is an integer from 1 to 5, the individual atoms or groups being identical or different when m is greater than 1, W is a group of the formula $(CH_2)_v$—$CR^1$=$CR^2$—$(CH_2)_t$, where $R^1$ and $R^2$ are identical or different and are each hydrogen, methyl, ethyl, chlorine or fluorine, or is a group of the formula $(CH_2)_v$—C≡C—$(CH_2)_t$, and v and t are identical or different and are each 1, 2 or 3, Z is CH or N, and Y is C=O or $CR^3OR^4$, where $R^3$ is hydrogen, methyl, vinyl, allyl, ethynyl or propynyl, and $R^4$ is hydrogen, $C_1$-$C_4$-alkyl, $C_2$-$C_4$-alkenyl, $C_2$-$C_4$-alkynyl or $C_2$-$C_4$-alkanoyl, or a plant-tolerated acid addition salt or metal complex thereof.

4. A compound of the formula I as set forth in claim 1, where V is oxygen, X is hydrogen or fluorine, W is —$CH_2$—CH=CH—$CH_2$—, Z is nitrogen, and Y is CO or CHOH.

* * * * *